US009440074B2

(12) United States Patent
Ternes et al.

(10) Patent No.: US 9,440,074 B2
(45) Date of Patent: Sep. 13, 2016

(54) METHOD AND SYSTEM FOR INDICATING NEUROSTIMULATION DELIVERY

(71) Applicant: Cardiac Pacemakers, Inc., St. Paul, MN (US)

(72) Inventors: David J. Ternes, Roseville, MN (US); Scott Vanderlinde, Plymouth, MN (US); Kevin G. Wika, Blaine, MN (US); Jonathan H. Kelly, Woodbury, MN (US); Rajeev Madhukar Sahasrabudhe, Maple Grove, MN (US); James Kalgren, Lino Lakes, MN (US); Rezwan Ahmed, Arden Hills, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 28 days.

(21) Appl. No.: 14/181,181

(22) Filed: Feb. 14, 2014

(65) Prior Publication Data

US 2014/0236261 A1  Aug. 21, 2014

Related U.S. Application Data

(60) Provisional application No. 61/765,843, filed on Feb. 18, 2013.

(51) Int. Cl.
*A61N 1/00* (2006.01)
*A61N 1/36* (2006.01)
*A61N 1/372* (2006.01)

(52) U.S. Cl.
CPC ....... *A61N 1/36053* (2013.01); *A61N 1/36128* (2013.01); *A61N 1/37235* (2013.01);

(Continued)

(58) Field of Classification Search
CPC .................. A61N 1/36503; A61N 1/36114; A61N 1/36167; A61N 1/36128; A61N 1/36135; A61N 1/3606; A61N 1/37258; A61N 1/37235; A61N 1/37264
See application file for complete search history.

(56) References Cited

U.S. PATENT DOCUMENTS 7,640,057 B2   12/2009   Libbus et al.
2006/0241725 A1   10/2006   Libbus et al.
(Continued)

FOREIGN PATENT DOCUMENTS

CN   101385890   3/2009
JP   2008538996   11/2008
(Continued)

OTHER PUBLICATIONS

"Communication Pursuant to Rules 161(1) and 162 EPC," for European Patent Application No. 147070718., mailed on Sep. 25, 2015 (2 pages).

(Continued)

*Primary Examiner* — Mallika D Fairchild
(74) *Attorney, Agent, or Firm* — Pauly, DeVries Smith & Deffner, LLC

(57) ABSTRACT

A method and system for providing an indication of delivery of a neural stimulation therapy is disclosed. In an example, a method may include identifying current timing of an intermittent neural stimulation (INS) programmed in an implantable medical device (IMD) where the programmed INS includes alternating stimulation ON and stimulation OFF times and a timing for delivering stimulation bursts of a plurality of stimulation pulses during the stimulation burst ON times. An indication of the current timing of the INS may be provided using an INS indicator of an external device.

20 Claims, 6 Drawing Sheets

(52) U.S. Cl.
CPC ......... *A61N1/37264* (2013.01); *A61N 1/3606* (2013.01); *A61N 1/36167* (2013.01); *A61N 1/37258* (2013.01)

(56) References Cited

U.S. PATENT DOCUMENTS

| | | | |
|---|---|---|---|
| 2007/0055318 A1 | 3/2007 | Forsberg et al. | |
| 2007/0055322 A1 | 3/2007 | Forsberg et al. | |
| 2008/0058874 A1* | 3/2008 | Westlund et al. | 607/2 |
| 2011/0015702 A1 | 1/2011 | Ternes et al. | |
| 2011/0137360 A1 | 6/2011 | Ternes et al. | |
| 2011/0257509 A1* | 10/2011 | Olsen et al. | 600/411 |
| 2011/0257708 A1 | 10/2011 | Kramer et al. | |
| 2011/0313488 A1 | 12/2011 | Hincapie Ordonez et al. | |

FOREIGN PATENT DOCUMENTS

| | | |
|---|---|---|
| JP | 2009233024 | 10/2009 |
| WO | 2009035515 | 3/2009 |
| WO | 2014127254 | 8/2014 |

OTHER PUBLICATIONS

"International Preliminary Report on Patentability," for PCT/US2014/016517 mailed Aug. 27, 2015 (6 pages).

"International Search Report and Written Opinion," for PCT/US2014/016517, mailed Apr. 9, 2014 (8 pages).

"Response to Communication Pursuant to Rules 161 and 162 EPC," for European Patent Application No. 147070718., filed with the EPO Jan. 13, 2016 (25 pages).

First Office Action, for Chinese Patent Application No. 201480005915.X mailed Mar. 9, 2016 (15 pages) with English translation.

Office Action, for Japanese Patent Application No. 2015-551075 mailed Jun. 7, 2016 (4 pages) with English translation.

\* cited by examiner

METHOD AND SYSTEM FOR INDICATING NEUROSTIMULATION DELIVERY

CLAIMS OF PRIORITY

This application claims the benefit of priority under 35 U.S.C. §119(e) of U.S. Provisional Patent Application Ser. No. 61/765,843, filed on Feb. 18, 2013, which is herein incorporated by reference in its entirety.

TECHNICAL FIELD

This document relates generally to neural stimulation and, more particularly, but not by way of limitation, to a method and system for indicating delivery of neural stimulation.

BACKGROUND

Neural stimulation, such as vagus nerve stimulation, has been proposed as a therapy for a number of conditions. Examples of neural stimulation therapies include neural stimulation therapies for respiratory problems such as sleep disordered breathing, blood pressure control such as to treat hypertension, cardiac rhythm management, myocardial infarction and ischemia, heart failure (HF), epilepsy, depression, pain, migraines, eating disorders and obesity, and movement disorders.

Vagus nerve stimulation can cause vibration of larynx. Thus, laryngeal activity can be used as an indication that the vagus nerve is being capture by the neural stimulation. For example, a clinician can physically touch the neck region of the patient to feel vibration of the larynx and confirm capture of the vagus nerve. However, physically touching the patient to monitor for laryngeal vibration can cause patient discomfort, particularly if longer periods of time are required to monitor for laryngeal vibration.

SUMMARY

Various embodiments of the present subject matter provide an indication of the neural stimulation status to a clinician or other person. For example, the indication may indicate whether the intermittent stimulation is in the stimulation ON state or in the stimulation OFF state. An implantable vagal nerve stimulator is discussed in this document as a specific example. Thus, for example, a clinician is able to use the indication to know when to touch a patient to monitor for laryngeal vibration.

A vagal nerve stimulation therapy may be intermittently delivered, where neural stimulation energy is delivered during stimulation ON periods of time, and where successive stimulation ON periods of time are separated by a stimulation OFF period of time where neural stimulation is not delivered. That is, the stimulation ON and stimulation OFF states alternate. Intermittent vagal nerve stimulation can be problematic for a clinician to verify capture because the clinician does not know if the sensed laryngeal vibration is attributable to the stimulation. Intermittent vagal nerve stimulation can be problematic for a physician to verify capture because the physician does not know if the sensed laryngeal vibration only occurs during the stimulation ON and thus is caused by the stimulation. However, the present subject matter may be practiced with other neural stimulation devices.

In an example of a system for providing an indication of delivery of intermittent neural stimulation (INS) to the vagus nerve, the system may include an implantable medical device (IMD) that can be configured to deliver programmed INS to the vagus nerve. The programmed INS can include alternating stimulation ON and stimulation OFF times and a timing for delivering stimulation bursts of a plurality of stimulation pulses during the stimulation burst ON times. An external device may be configured to identify a current timing of the INS delivered by the IMD. The external device can include an INS indicator configured to provide a user-perceptible indication of the current timing of the programmed INS.

In an example of a method for providing an indication of a current timing of an intermittent neural stimulation (INS), the method may include identifying the current timing of the INS being programmed in an implantable medical device (IMD). The programmed INS can include alternating stimulation ON and stimulation OFF times and a timing for delivering stimulation bursts of a plurality of stimulation pulses during the stimulation burst ON times. An indication of the current timing of the INS may be provided using an INS indicator of an external device.

In an example of a method for verifying the capture of a vagus nerve, the method may include delivering intermittent neural stimulation (INS) to the vagus nerve, where the INS is programmed in an implantable medical device (IMD). The programmed INS can include alternating stimulation ON and stimulation OFF times and a timing for delivering stimulation bursts of a plurality of stimulation pulses during the stimulation burst ON times. An external device may be monitored for an indication of the current timing of the INS. The method may include monitoring for laryngeal vibrations and using monitored laryngeal vibration results and the indication of the current timing of the INS to determine if the INS is capturing the vagus nerve. The method may include determining that the INS is not capturing the vagus nerve if laryngeal vibration is not detected and the current timing of the INS is stimulation ON.

This Summary is an overview of some of the teachings of the present application and is not intended to be an exclusive or exhaustive treatment of the present subject matter. Further details about the present subject matter are found in the detailed description and appended claims. The scope of the present invention is defined by the appended claims and their equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
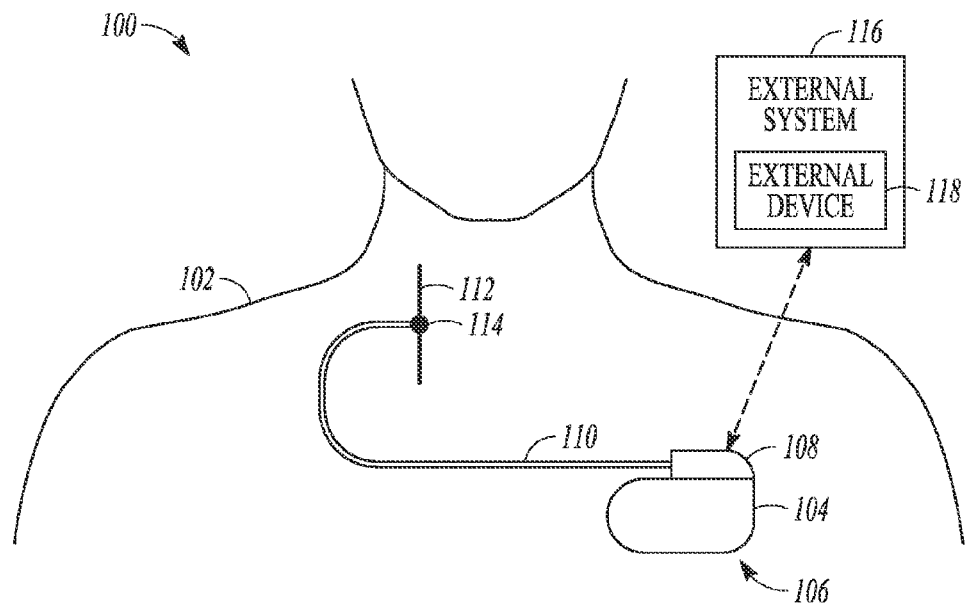
FIG. 1 illustrates, by way of example, an embodiment of a neural stimulation system.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Disclosed herein are methods and systems for indicating delivery of neural stimulation. The indication of neural stimulation delivery may be useful to verify capture of a neural target, to titrate the intensity of the neural stimulation therapy to a desired dose, or to both verify capture and titrate. Without such an indication, it can be difficult to determine when to sense for a response to the stimulation, and to determine whether the observed response is attributable to the stimulation or to another event. These indications are desirable when the neural stimulation is delivered as an INS therapy. A programmed INS therapy may be programmed to provide a burst of neural stimulation pulses during stimulation ON times, and to separate stimulation ON times with stimulation OFF times.

In an example, the neural stimulation is directed to stimulating the autonomic nervous system, which is discussed herein as a particular example. For example, the neural stimulation may be directed to stimulating a vagus nerve in the neck (e.g. cervical vagus nerve) or to stimulating various nerves that branch from the vagus nerve trunk. The neural stimulation may be directed to other autonomic nervous system targets. Examples of other autonomic neural stimulation targets include but are not limited to baroreceptor regions in the carotid sinus region or in the pulmonary artery, the glossopharyngeal nerve, the carotid sinus nerve, and spinal nerves. However, the present subject matter is not so limited, as the neural stimulation may be directed to other sites where it would be desirable to provide an indication of neural stimulation. For example, it may be desirable to provide an indication of neural stimulation for a neural stimulator configured to stimulate the target in the somatic system in order to determine if muscle movements (whether intended or not intended) are attributable to the stimulation of the somatic system. As a more specific example, it has been proposed to stimulate the hypoglossal nerve which innervates muscles in the tongue, such as to provide a treatment for obstructive sleep apnea. The present subject matter may be implemented to monitor the delivery of neural stimulation to the hypoglossal nerve, allowing the clinician to confirm that tongue motion is attributable to the neural stimulation.

The autonomic nervous system (ANS) regulates "involuntary" organs, while the contraction of voluntary (skeletal) muscles is controlled by somatic motor nerves. Examples of involuntary organs include respiratory and digestive organs, and also include blood vessels and the heart. Often, the ANS functions in an involuntary, reflexive manner to regulate glands, to regulate muscles in the skin, eye, stomach, intestines and bladder, and to regulate cardiac muscle and the muscles around blood vessels, for example.

The ANS includes the sympathetic nervous system and the parasympathetic nervous system. The sympathetic nervous system is affiliated with stress and the "fight or flight response" to emergencies. Among other effects, the "fight or flight response" increases blood pressure and heart rate to increase skeletal muscle blood flow, and decreases digestion to provide the energy for "fighting or fleeing." The parasympathetic nervous system is affiliated with relaxation and the "rest and digest response" which, among other effects, decreases blood pressure and heart rate, and increases digestion to conserve energy. The ANS maintains normal internal function and works with the somatic nervous system. Afferent neurons convey impulses towards the central nervous system (CNS), and efferent neurons convey impulses away from the CNS.

Stimulating the sympathetic and parasympathetic nervous systems can cause heart rate, blood pressure and other physiological responses. For example, stimulating the sympathetic nervous system dilates the pupil, reduces saliva and mucus production, relaxes the bronchial muscle, reduces the successive waves of involuntary contraction (peristalsis) of the stomach and the motility of the stomach, increases the conversion of glycogen to glucose by the liver, decreases urine secretion by the kidneys, and relaxes the wall and closes the sphincter of the bladder. Stimulating the parasympathetic nervous system (inhibiting the sympathetic nervous system) constricts the pupil, increases saliva and mucus production, contracts the bronchial muscle, increases secretions and motility in the stomach and large intestine, increases digestion in the small intestine, increases urine secretion, and contracts the wall and relaxes the sphincter of the bladder. The functions associated with the sympathetic and parasympathetic nervous systems are many and can be complexly integrated with each other. A therapy which intentionally affects the parasympathetic activity and/or sympathetic activity within the ANS may be referred to as an Autonomic Modulation Therapy (AMT). A neural stimulation therapy delivered to an autonomic neural target is an example of an AMT. The vagus nerve is an example of an autonomic neural target. For example, the cervical vagus nerve may be stimulated to treat conditions such as, by way of example and not limitation, hypertension, heart failure, arrhythmias and pain. Other examples of conditions that may be treatable using vagus nerve stimulation include, but are not limited to, migraines, eating disorders, obesity, inflammatory diseases, and movement disorders. Other autonomic neural targets include, but are not limited to, baroreceptor regions, chemoreceptor regions, cardiac fat pads, various branches of the vagus nerve, the carotid sinus nerve, and the glossopharyngeal nerve.

A reduction in parasympathetic nerve activity contributes to the development and progression of a variety of cardiovascular diseases. Some embodiments of the present subject matter can be used to prophylactically or therapeutically treat various cardiovascular diseases by modulating autonomic tone. Neural stimulation to treat cardiovascular diseases may be referred to as neurocardiac therapy (NCT). Vagal stimulation used to treat cardiovascular diseases may be referred to as either vagal stimulation therapy (VST) or NCT. However, VST may be delivered for non-cardiovascular diseases, and NCT may be delivered by stimulating a nerve other than the vagal nerve. Examples of cardiovascular diseases or conditions that may be treated using AMT include hypertension, HF, and cardiac remodeling. These conditions are briefly described below.

Hypertension is a cause of heart disease and other related cardiac co-morbidities. Hypertension occurs when blood vessels constrict. As a result, the heart works harder to maintain flow at a higher blood pressure, which can contribute to HF. Hypertension generally relates to high blood pressure, such as a transitory or sustained elevation of systemic arterial blood pressure to a level that is likely to induce cardiovascular damage or other adverse consequences. Hypertension has been defined as a systolic blood pressure above 140 mm Hg or a diastolic blood pressure above 90 mm Hg. Consequences of uncontrolled hypertension include, but are not limited to, retinal vascular disease and stroke, left ventricular hypertrophy and failure, myocardial infarction, dissecting aneurysm, and renovascular disease. A large segment of the general population, as well as a large segment of patients implanted with pacemakers or defibrillators, suffer from hypertension. The long term mortality as well as the quality of life can be improved for this population if blood pressure and hypertension can be reduced. Many patients who suffer from hypertension do not respond to treatment, such as treatments related to lifestyle changes and hypertension drugs.

HF refers to a clinical syndrome in which cardiac function causes a below normal cardiac output that can fall below a level adequate to meet the metabolic demand of peripheral tissues. HF may present itself as congestive heart failure (CHF) due to the accompanying venous and pulmonary congestion. HF can be due to a variety of etiologies such as ischemic heart disease. HF patients have impaired autonomic balance, which is associated with LV dysfunction and increased mortality.

Cardiac remodeling refers to a complex remodeling process of the ventricles that involves structural, biochemical, neurohormonal, and electrophysiologic factors, which can result following a myocardial infarction (MI) or other cause of decreased cardiac output. Ventricular remodeling is triggered by a physiological compensatory mechanism that acts to increase cardiac output due to so-called backward failure which increases the diastolic filling pressure of the ventricles and thereby increases the so-called preload (i.e., the degree to which the ventricles are stretched by the volume of blood in the ventricles at the end of diastole). An increase in preload causes an increase in stroke volume during systole, a phenomena known as the Frank-Starling principle. When the ventricles are stretched due to the increased preload over a period of time, however, the ventricles become dilated. The enlargement of the ventricular volume causes increased ventricular wall stress at a given systolic pressure. Along with the increased pressure-volume work done by the ventricle, this acts as a stimulus for hypertrophy of the ventricular myocardium. The disadvantage of dilatation is the extra workload imposed on normal, residual myocardium and the increase in wall tension (Laplace's Law) which represent the stimulus for hypertrophy. If hypertrophy is not adequate to match increased tension, a vicious cycle ensues which causes further and progressive dilatation. As the heart begins to dilate, afferent baroreceptor and cardiopulmonary receptor signals are sent to the vasomotor central nervous system control center, which responds with hormonal secretion and sympathetic discharge. The combination of hemodynamic, sympathetic nervous system and hormonal alterations (such as presence or absence of angiotensin converting enzyme (ACE) activity) account for the deleterious alterations in cell structure involved in ventricular remodeling. The sustained stresses causing hypertrophy induce apoptosis (i.e., programmed cell death) of cardiac muscle cells and eventual wall thinning which causes further deterioration in cardiac function. Thus, although ventricular dilation and hypertrophy may at first be compensatory and increase cardiac output, the processes ultimately result in both systolic and diastolic dysfunction. It has been shown that the extent of ventricular remodeling is positively correlated with increased mortality in post-MI and heart failure patients.

Nerve cuffs may be used to stimulate the vagus nerve. Transvascularly stimulating the vagus nerve using electrodes in a blood vessel such as the internal jugular vein is less invasive. Another less invasive means for stimulating the vagus nerve includes stimulating the vagus nerve using electrodes placed proximate to the nerve within the carotid sheath. Verifying vagus nerve capture is desirable for cuff and non-cuff electrode arrangements. Verifying vagus nerve capture may also be relevant for automatic titration in both cuff and non-cuff electrode arrangements.

A branch of the vagus nerve is the recurrent laryngeal nerve, which innervates the laryngeal muscles. The vagus nerve is stimulated at a stimulation site more cranial than the position where the recurrent laryngeal nerve branches off of the vagus nerve. Stimulation that captures the vagus nerve at this stimulation site enhances efferent vagal nerve traffic from this position, propagating action potentials through the recurrent laryngeal nerve and causing laryngeal muscle activation. Various embodiments of the present subject matter deliver vagal stimulation to enhance efferent vagal nerve traffic, and detect activation of the laryngeal muscles to provide feedback to a clinician during the implantation procedure, to provide feedback to a clinician during patient follow-ups, or to provide feedback for auto-titration routines intermittently performed in an implanted device.

VST may include stimulation to increase vagus nerve traffic, stimulation to block or reduce vagus nerve traffic, unidirectional stimulation of the vagus nerve (e.g. stimulation that significantly affects nerve traffic in the afferent direction but not the efferent direction, or stimulation that significantly affects nerve traffic in the efferent direction but not the afferent direction), or stimulation that is non-unidirectional (e.g. stimulation that significantly affects nerve traffic in both the afferent and efferent direction). Therefore, the VST delivered from the stimulation electrodes for the therapy may enhance efferent vagal nerve traffic after vagus nerve capture is verified or the therapy is titrated. However, the present subject matter may be used to verify vagus nerve capture, and then provide a VST that does not enhance efferent vagal nerve activity. For example, the device may be configured to block efferent vagal nerve activity or to deliver VST to unidirectionally enhance afferent vagus nerve activity after vagus nerve capture is verified. The parameters used to verify vagus nerve capture can be used to determine the appropriate VST parameters, whether the VST is configured to increase afferent or efferent nerve traffic either unidirectionally or non-unidirectionally, or whether the VST is configured to block or decrease efferent nerve traffic, afferent nerve traffic or both efferent and afferent nerve traffic.

FIG. 1 illustrates, by way of example, an embodiment of a neural stimulation system 100 and an environment in which the neural stimulation system 100 can be used. The neural stimulation system 100 can be configured to deliver a neural stimulation therapy to one or more bodily tissues of a patient 102 such as to a cervical vagus nerve. In an example, the neural stimulation system 100 can be configured to include an implantable medical device (IMD) 104 that can be programmed to deliver a programmed intermittent neural stimulation (INS) to one or more nerves of the patient 102.

As illustrated in FIG. 1, the IMD 104 can include a hermetically-sealed housing 106. The IMD 104 may include a header 108 extending from the housing 106, with one or more receptacles for receiving proximal ends of one or more leads such as lead 110. The distal end of the lead 110 can include one or more electrical contacts called "electrodes" for use in delivering the stimulation pulses to a vagus nerve 112 of the patient 102. For example, the distal end of the lead 110 can include an electrode 114 such as to deliver stimulation pulses to respective sites of the vagus nerve 112. The electrode may be configured as a nerve cuff configured to be placed at least partially around the nerve, or may be configured to be placed adjacent to the nerve for use to stimulate the nerve, or may be configured to be placed intravascularly near the nerve for use to transvascularly stimulate the nerve. Although the figure illustrates a single electrode, it is understood that more than one electrode may be operationally placed near the nerve to stimulate the nerve. Further it is understood that three or more electrodes may be used to control the electric field that stimulates the nerve. The stimulation may be bipolar stimulation where an anode and cathode are both near the nerve. The stimulation may be monopolar stimulation. For example, the housing 106 of the IMD 104 can include a reference electrode (e.g., a can electrode), and the neural stimulation can be delivered using the lead electrode 114 and the reference electrode of the housing 106.

The IMD 104 may be a stand-alone neural stimulator, or may be combined with other device such as, without limitation, myocardial stimulators. An example of a myocardial stimulator includes a cardiac pacemaker, a defibrillator, a cardiac resynchronization therapy (CRT) device, or a combination of such devices. The neural stimulation system 100 can be configured to include other monitoring or therapeutic devices (e.g., a drug delivery device, a biological therapy device, or other device). In an example, the IMD 104 can be configured to communicate with other implantable medical devices (not illustrated), such as another implanted neural stimulator or an implanted myocardial stimulator. In an example, the IMD 104 can be configured to communicatively couple to an external system 116 through a wireless or a wired link. For example, the wireless link can be an inductive telemetry link or a far-field radio frequency telemetry link.

The external system 116 may include an external device 118 such as an IMD programmer that can enable a physician to program the IMD 104 for one or more programmable parameters such as neural stimulation parameters, threshold values (e.g., sensing threshold values), selection of one or more therapy modes, and others such as to provide an appropriate neural stimulation therapy to the patient 102 diagnosed with a specific disorder. In an example, the external system 116 may be a portion of a remote patient management system that can assist the physician to remotely monitor the status of the patient 102 on a real-time basis and thereby remotely adjust the neural stimulation therapy.

Various neural stimulation therapies include INS. The present system and methods can be configured to deliver programmed INS to the vagus nerve 112 of the patient 102. In an example, the programmed INS can include intermittently-delivered bursts of electrical pulses. For example, a plurality of electrical pulses may be delivered as a train of pulses during stimulation ON times. These trains of pulses are separated by a stimulation OFF time where the train of pulses is not delivered. The neural stimulation may be delivered using non-electrical forms of energy, such as mechanical, thermal, optical, and chemical, that capable of eliciting neural activities in the nervous system.

The present system and methods can be configured to provide indications to the physician regarding the stimulation ON time and the stimulation OFF time of the programmed INS. The physician can utilize these indications such as to determine presence of the laryngeal vibrations during the stimulation ON time. As a result, the physician can determine that the stimulation is capturing the vagus nerve 112 during the stimulation ON time. For example, the physician may sense for laryngeal vibration to verify capture of the cervical vagus nerve. Further, the physician can determine that the stimulation intensity is effective in achieving a desired physiological response. The neural stimulation intensity may also be considered to be a dose of neural stimulation (amount of charge delivered to the neural target over a period of time). For example, higher stimulation amplitudes deliver more charge and thus have a higher stimulation intensity. Wider pulse widths deliver more charge and thus have a higher stimulation intensity. Likewise, longer stimulation pulse duty cycles and longer stimulation ON duty cycles for a train of pulses delivered in an INS therapy also provide more charge over a period of time.

The indicator of stimulation ON time and stimulation OFF time are provided as a specific example of a neural stimulation state. The indicator alternatively or in addition be used to provide external indicator(s) of other neural stimulation states, which may reflect changes in therapy outputs such as changes in stimulation amplitude, frequencies, duty cycles, or other stimulation parameters. For example, a therapy may consist of x minutes at A amplitude followed by y minutes of B amplitude. The therapy may also have a stimulation OFF time following the y minutes of B amplitude, where a stimulation ON time includes the x minutes and y minutes. The indicator may be used to provide an outward indicator of two or more therapy states.

The programmed INS with a programmed stimulation ON time and a stimulation OFF time is also a specific example. However, the indicator disclosed herein may also be used to monitor for temporary neural stimulation that is triggered by an event. For example, the triggering event may be a respiratory phase, posture, activity, blood pressure, a shock from an ICD (implantable cardioverter-defibrillator). The device may be programmed to deliver the neural stimulation for a period of time after the triggering event. The indicator may provide an external indicator that confirms that stimulation is being delivered in response to the triggering event, and may also indicate the time until the stimulation stops.

Figure 2:
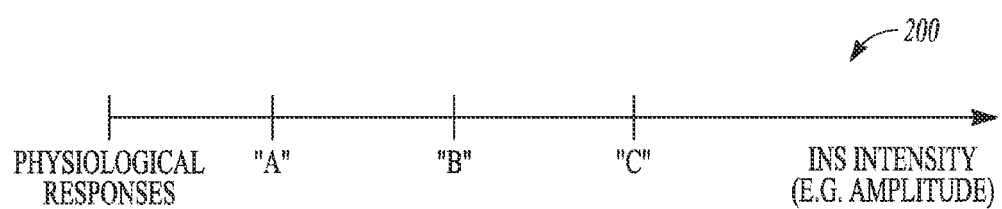
FIG. 2 illustrates, by way of example, increasing VST intensity from the left side to the right side of the figure, and further illustrates intensity thresholds that elicit various physiological responses to VST.

The vagus nerve is a complex physiological structure with many neural pathways that are recruited at different stimulation thresholds. Various physiological responses to vagal stimulation are associated with various thresholds of VST intensity. For example, FIG. 2 illustrates increasing VST intensity from the left side to the right side of the figure, and further illustrates intensity thresholds that elicit various physiological responses to VST. An example of increasing intensity is increasing amplitude. VST causes a physiological response "A" at a lower intensity than an intensity at which VST causes a physiological response "B", which occurs at a lower VST intensity than an intensity at which VST causes a physiological response "C". Stated another way, VST triggers response "A" after reaching a certain level, triggers response "B" along with response "A" after reaching a higher intensity, and triggers response "C" along with responses "A" and "B" after reaching an even higher intensity.

Physiological responses at lower VST intensities can have therapeutically-effective results for cardiovascular diseases such as HF. Lower VST intensities may also have therapeutically-effective results for other diseases. These responses mediate or provide pathways for these therapies. Examples of such responses that are beneficial for HF at the lower VST intensities include anti-inflammation, anti-sympathetic, and anti-apoptosis responses, and an increased nitric oxide (NO). Physiological responses at the higher VST intensities may not be desirable. Examples of responses to higher VST intensities that may reduce the ability of the patient to tolerate VST include, but are not limited to, reduced heart rate, prolonged AV conduction, vasodilation, and coughing. At least some of these responses may be desirable for some therapies but not desirable for other therapies. By way of example and not limitation, VST that reduces heart rate and or that prolongs AV conduction may be desirable to treat some cardiovascular diseases, but may not be desirable for other cardiovascular diseases. The intensity of the VST can be adjusted by adjusting parameter(s) of the stimulation signal. For example, the amplitude of the signal (e.g. current or voltage) can be increased to increase the intensity of the signal. Other stimulation parameter(s) can be adjusted as an alternative to or in addition to amplitude. For example, stimulation intensity can vary with the frequency of the stimulation signal (e.g. a frequency of stimulation pulses), a stimulation burst frequency (e.g. a plurality of bursts delivered at a burst frequency for initiating bursts where each burst includes a plurality of pulses), a pulse width and/or a duty cycle. Typical vagal nerve stimulation may have a signal amplitude of above 0.1-10 mA and a frequency of about 1-50 Hz.

Figure 3:
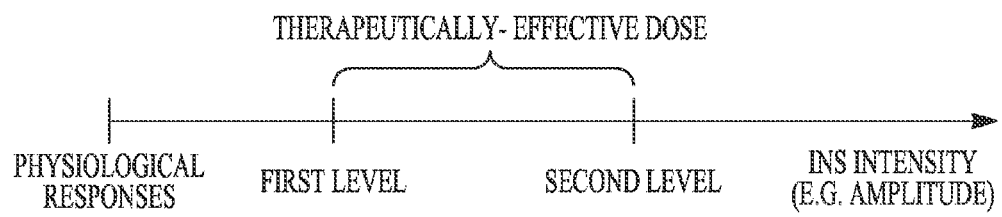
FIG. 3 illustrates increasing VST intensity from the left side to the right side of the figure, and further generally illustrates an example of boundaries for a therapeutically-effective dose.

FIG. 3 illustrates increasing VST intensity from the left side to the right side of the figure, and further generally illustrates an example of boundaries for a therapeutically-effective dose. A vagus nerve capture threshold can be set by confirming capture of the vagus nerve using laryngeal vibration. The stimulation parameters may be set based on the stimulation parameters that caused the laryngeal vibrations. For example, if the amplitude of the stimulation signal is increased to increase the VST intensity and if 1.0 mA caused laryngeal vibrations, then the pacing amplitude may be set to an offset value (x mA) above the laryngeal vibration threshold amplitude (e.g. 1 mA+x mA) or as a factor of the laryngeal vibration threshold (e.g. 1 mA*factor). Additionally, some embodiments may place an upper boundary on the VST. The upper boundary may be based on a detected undesired response to the stimulation, such as cough or undesired muscle stimulation.

Figure 4:
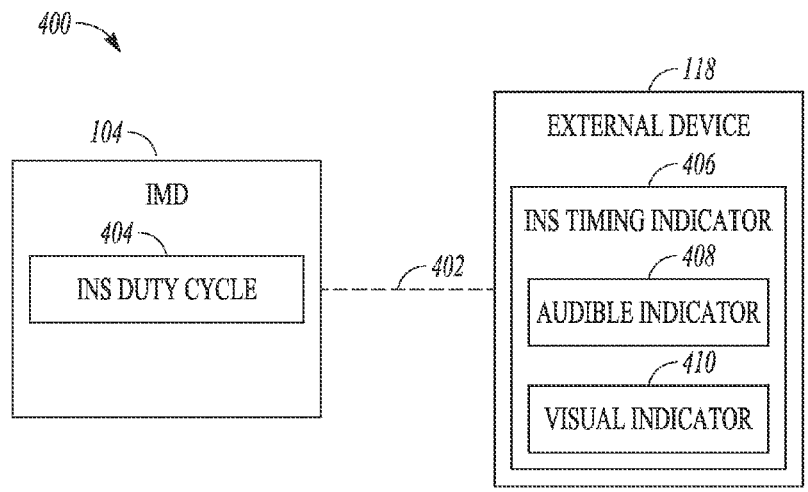
FIG. 4 illustrates, by way of example, an embodiment of a neural stimulation system for monitoring and delivering the neural stimulation to the patient.

FIG. 4 illustrates, by way of example, an embodiment of a neural stimulation system 400 for monitoring and delivering the neural stimulation to the patient 102. The illustrated neural stimulation system 400 includes an IMD 104 for delivering neural stimulation and an external device 118 for monitoring neural stimulation delivery. The IMD 104 can be configured to communicate with the external device 118 through a telemetry link 402. By way of example, the IMD 104 can be configured to deliver programmed INS to the vagus nerve 112 of the patient 102. For example, the IMD 104 is capable of being programmed to store INS parameters, such as information associated with an INS duty cycle 404. Programmed INS duty cycle parameters control the stimulation ON/stimulation OFF timing of an INS therapy. The external device 118 can be configured to include an INS timing indicator 406 that can be configured to provide an indication of the stimulation ON/stimulation OFF timing associated with the INS being delivered by the IMD 104. The IMD 104 can be configured to communicate the information associated with the INS duty cycle 404 to the external device 118. This information may include the programmed duration for stimulation ON, the programmed duration for stimulation OFF, the programmed total duration for the stimulation ON and OFF which may also be referred to as a burst period, or various combination thereof. Furthermore, the information may include timing reference points for the INS duty cycle, such as a reference point or points for the start and/or end of the stimulation ON time which correspond to the end and/or start of the stimulation OFF time. The INS duty cycle parameters may also include, in some examples, ramp up parameters for controlling the transition from the stimulation OFF time to the stimulation ON time and/or ramp down parameters for controlling the transition from the stimulation ON time to the stimulation OFF time. The external device 118 can be configured to indicate the current timing of the INS duty cycle 404 as received from the IMD 104 to the physician using the INS timing indicator 406.

In various examples, the INS timing indicator 406 can be configured to include an audible indicator 408, a visual indicator 410, or both for providing a user-perceptible indication or indications of the current INS timing. In an example, the INS timing indicator 406 can provide a user-perceptible indication of the status of the duty cycle of the INS. In other examples, the INS timing indicator 406 can provide a user-perceptible indication of various other parameters of the programmed INS.

In an example, the user-perceptible indication can be an audible indication as provided by the audible indicator 408 of the INS timing indicator 406. Examples of such audible indication can include, but are not limited to, a continuous tone, a beep, a music note or notes, a voice recording, audio patterns and other audio signals. In an example, the audible indication can include a distinct tone or a sound to indicate the current timing such as the stimulation ON time or the stimulation OFF time of the programmed INS. In an example, audible indicator 408 may not generate an audible signal when the neural stimulation therapy is disabled, may generate a continuous audible signal during the stimulation ON time of the programmed INS, and may generate an intermittent audio signal during the stimulation OFF time of the programmed INS. In an example, the intermittent audio signal can be used with an intermittent visual signal such as an intermittent light signal. In this combination, a frequency of the intermittency of the audible and light signal can be increased when the programmed INS is about to make a transition from stimulation OFF time to the stimulation ON time.

In an example, the user-perceptible indication can be a visual indication as provided by the visual indicator 410 of the INS timing indicator 406. In an example, a light emitting device such as a light emitting diode (LED) or any other may provide the visual indicator 410. The light emitting device can emit different colors corresponding to different timings of the programmed INS. For example, a red light is emitted when the programmed INS is disabled, a green light is emitted when the programmed INS is enabled and the current timing of the programmed INS is the stimulation ON time, and a yellow light is emitted when programmed INS is enabled and the current timing of the programmed INS is the stimulation OFF time. Furthermore, the color for a state may change or the visual indicator otherwise adapted as the time approaches for a transition (e.g. stimulation ON to stimulation OFF or stimulation OFF to stimulation ON). In an example, different colors of light are shown on a graphical interface of the external device 118 in the form of a circle or a slash. Examples of the visual indications can include, but are not limited to, waveform visualization, a counter visualization, clock face visualization, timer visualization, and other visual indications. In an example, the user-perceptible indication for the current timing of the programmed INS can be used by the physician such as during a clinical titration procedure to assess effectiveness of the neural stimulation therapy delivered to the patient 102. For example, the physician can use the indication of the current INS timing in combination with manual sensing of the patient's neck for laryngeal vibration to assess nerve capture.

Figure 5A:
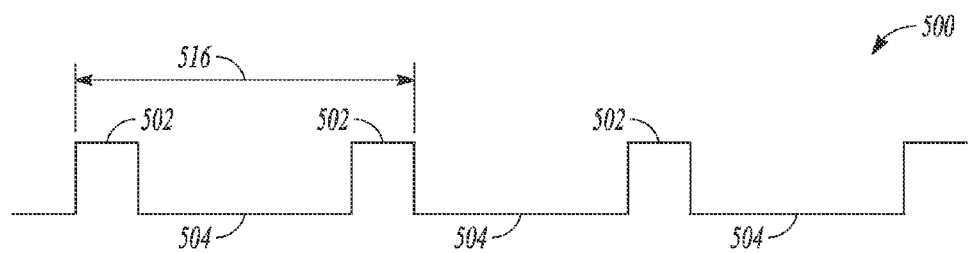
FIGS. 5A and 5B illustrate, by way of example, a representation of INS.
Figure 5B:
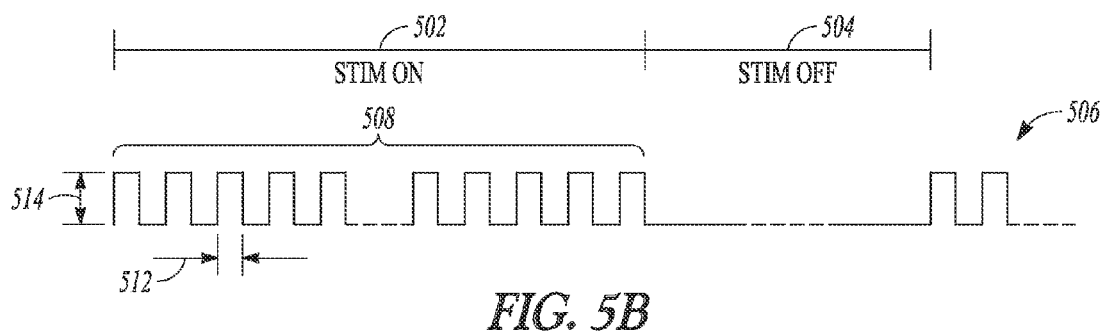

FIGS. 5A and 5B illustrate a representation of INS. The figure diagrammatically shows the time-course of a neural stimulation that alternates between intervals of stimulation being ON 502, when a burst or train of stimulation pulses 508 is delivered, and intervals of stimulation being OFF 504 when no stimulation pulses are delivered. Thus, for example, some embodiments deliver a plurality of monophasic or biphasic pulses within a neural stimulation burst 508 illustrated in FIG. 5. The neural stimulation can be generated using a plurality of parameters for which the IMD 104 can be programmed. Pulses delivered within a burst 508 may be delivered at a pulse frequency. A pulse period is the time between successive pulses. These pulses have a pulse width 512 and an amplitude 514. Both the pulse frequency and the pulse amplitude affect the dose of the neural stimulation therapy as they affect the amount of charge delivered to the tissue over a period of time. The duration of the stimulation ON interval is sometimes referred to as the stimulation duration or burst duration. The burst duration also affects the dose of the neural stimulation therapy. The start of a stimulation ON interval may be a temporal reference point "NS Event." The time interval between successive NS Events is the INS Interval, may be referred to as the stimulation period or burst period 516. The burst period 516 or the number of neural stimulation events that occur over a time period also affect the dose of the neural stimulation. For an application of neural stimulation to be intermittent, the stimulation duration (i.e., ON interval) is less than the stimulation period (i.e., INS Interval). The duration of the ON interval relative to the INS Interval (e.g., expressed as a ratio) is sometimes referred to as the duty cycle of the INS.

A clinician may control the adjustment of one or more neural stimulation parameters to control the stimulation intensity. For example, during an implantation procedure in which stimulation electrodes are implanted near a neural target such as a vagus nerve, clinician may adjust stimulation parameter(s) to program the stimulation with an appropriate dose to provide threshold stimulation of the neural target that provides a desired physiological effect. For example, if the neural target is a cervical vagus nerve, a desired physiological effect may be laryngeal vibrations caused by the stimulation of the vagus nerve cranially to the position where the laryngeal nerve branches from the vagus nerve. The clinician may re-program an implantable neural stimulator during a follow-up visit, to account for migration of the electrodes, changes in impedance in the electrode/tissue interface, and the like. During the follow-up visit, the clinician may control the adjustment of one or more neural stimulation parameters to control the stimulation intensity to determine a neural stimulation intensity that provides the desired physiological response.

In an example, the IMD 104 can be programmed to deliver the programmed INS. By way of example and not limitation, the IMD 104 may be programmed with INS duty cycle having value lesser than 50%. In an example, the IMD 104 may be programmed with a stimulation ON time about 10 seconds (e.g. within a range of about 5 seconds to 15 seconds) and a stimulation OFF time about 50 seconds (e.g. within a range of about 40 seconds to 70 seconds). The range about the 10 second ON time and the range about the 50 second OFF time may be larger or may be smaller, according to various embodiments. These are examples of ON/OFF timing for neural stimulation. The ON/OFF timing may be different for a specific therapy. For example, a condition may be treated with an INS duty cycle larger than 50%, such as an ON time on the order of minutes and an OFF time on the order of seconds.

Figure 6:
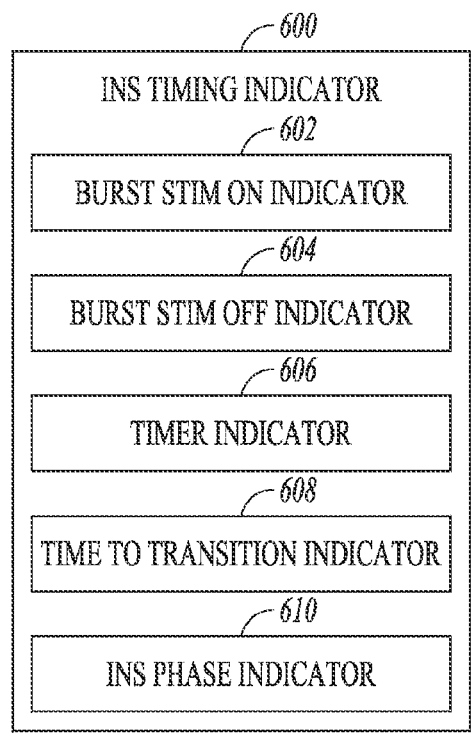
FIG. 6 illustrates, by way of example, an embodiment of an INS timing indicator for use in an external device of the neural stimulation system.

FIG. 6 illustrates, by way of example, an embodiment of an INS timing indicator 600 such as may be used in an external device. The INS timing indicator provides an indication of at least one time for the programmed INS. In an example, the INS timing indicator 600 can include a burst stimulation ON indicator 602. The burst stimulation ON indicator 602 may be configured to indicate to the physician that the programmed INS is currently in the stimulation ON time 502. In an example, the INS timing indicator 600 can include a burst stimulation OFF indicator 604. The burst stimulation OFF indicator 604 may be configured to indicate to the physician that the programmed INS is currently in the stimulation OFF time 504 of the INS duty cycle 404. In an example, the INS timing indicator 600 can include a timer indicator 606. The timer indicator 606 may be configured to indicate the time until the next stimulation ON time 502 or until the next stimulation OFF time 504. For example, the timer indicator 606 can provide a numeral indication on a display where the numeral on the display represents the remaining duration (e.g., milliseconds, seconds, or minutes) until the next stimulation ON time 502 or the next stimulation OFF time 504. In an example, the INS timing indicator 600 can include a time to transition indicator 608. The time to transition indicator 608 can be configured to indicate when the programmed INS transitions between the stimulation ON time 502 and the stimulation OFF time 504. In an example, the INS timing indicator 600 can include an INS phase indicator 610. In an example, the programmed INS can include a cycle of the stimulation ON time 502 and the stimulation OFF time 504. In an example, the INS phase indicator 610 can be configured to indicate the phase of the stimulation cycle of the programmed INS. In various examples, the INS timing indicator includes any two or more of a burst stimulation ON indicator, a burst stimulation OFF indicator, a timer indicator, a time to transition indicator, and an INS phase indicator. In an example, the external device 118 is configured to provide a visual or audible indication of the current timing of the programmed INS using any of the indicators discussed above.

In an example, the IMD 104 can be programmed to deliver the programmed INS. By way of example and not limitation, the IMD 104 may be programmed with INS duty cycle having value lesser than 50%. Further, by way of example and not limitation, the IMD 104 may be programmed with a stimulation ON time about 10 seconds (e.g. within a range of about 5 seconds to 15 seconds) and a stimulation OFF time about 50 seconds (e.g. within a range of about 30 seconds to 70 seconds). However, these ranges may be larger or may be smaller, according to various embodiments. The indication of neural stimulation status may be implemented with a variety of neural stimulation protocols.

Figure 7:
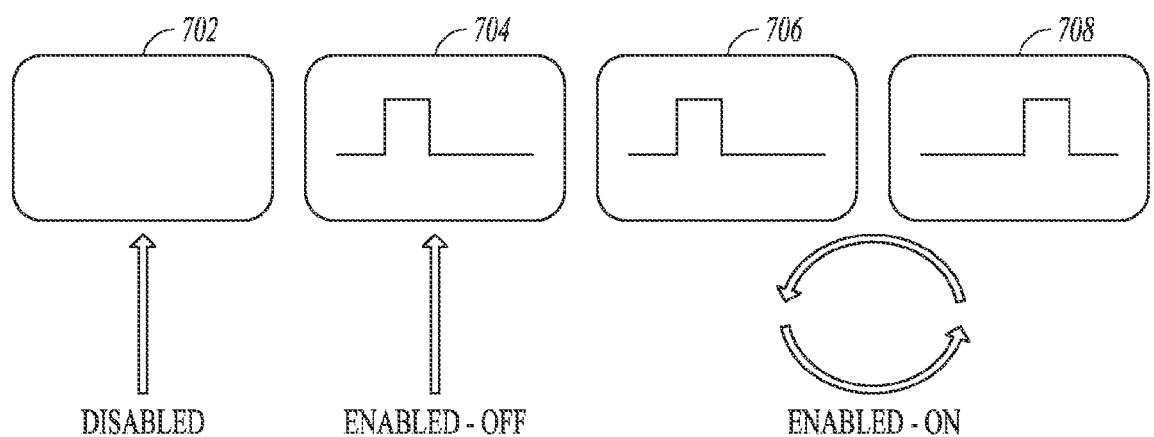
FIG. 7 illustrates, by way of example, an embodiment of a visual indication to depict timing of a neural stimulation therapy such as a programmed INS.

FIG. 7 illustrates an example of a visual indication 700 that may be provided to the clinician during delivery of a neural stimulation therapy such as a programmed INS. In an example, the visual indication can be configured to show corresponding timings of the programmed INS. For example, a blank screen such as shown in a display 702 may be presented to the clinician to indicate that a neural stimulation therapy is disabled. In an example, a static waveform such as shown in a display 704 can be presented to the clinician when the delivery of the programmed INS is enabled with the INS in the stimulation OFF time. In an example, the visual indication can display moving waveforms, such as generally illustrated by displays 706 and 708, when the programmed INS is enabled with the current timing of the programmed INS in the stimulation ON time.

Figure 8A:
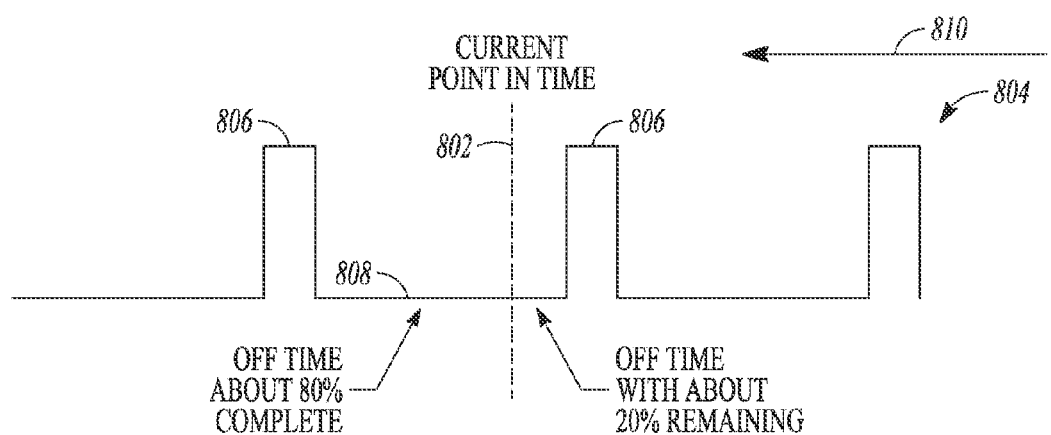
FIGS. 8A-8B illustrate, by way of examples, some embodiments of a visual indication to depict timing of a neural stimulation therapy such as a programmed INS.
Figure 8B:
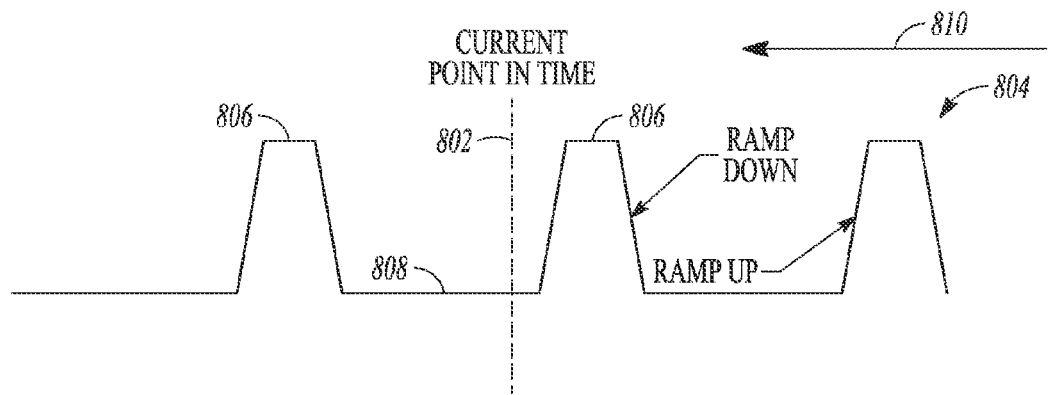

FIGS. 8A-8B illustrate some examples of a visual indication that may be provided to the clinician to depict timing of a neural stimulation therapy such as a programmed INS. In an example, a marker 802 may be used to convey duty cycle information to the clinician. The marker 802 can be used to indicate current timing of the programmed INS within the duty cycle(s) of the programmed INS. The relative position of the marker 802 with respect to a waveform 804 illustrating the INS stimulation ON times 806 and stimulation OFF times 808 may be used to represent a current state of the INS duty cycle. In an example, the display may provide a static marker 802 and a moving waveform 804. For example, the waveform 804 may move. The moving waveform may, for example, move in a direction as indicated by an arrow 810 to appropriately locate the waveform 804 with respect to the marker location for the duty cycle timing. In other example, the display may provide a static waveform 804 and a moving marker 802 can be configured to move. The moving marker may, for example, move in an opposite direction as the direction indicated by the arrow 810. An intersection of marker 802 with the waveform 804 at a particular point of time can indicate the current timing of the programmed INS. As an example, in FIG. 8A, the intersection of the marker 802 and the waveform 804 indicates that currently the duty cycle of the programmed INS is in the stimulation OFF time/state. It also provides an illustration of a time until the next transition. For example, FIG. 8A illustrates that about 80% of the Stimulation OFF time 808 has been completed, and that about 20% of the programmed stimulation OFF time remains until the waveform 804 transitions to the next stimulation ON time 806. Thus, if the programmed OFF time is 50 seconds for example, the physician will recognize that the next stimulation ON time will occur in about 10 seconds (20% of 50 seconds). Some display embodiments may also display a time (e.g. a quantity such as seconds or a percentage of a stimulation state) left until a duty cycle transition along with the marker 802 and waveform 804 illustrated in FIG. 8A. In some display examples, the display is configured to allow the clinician to zoom in to view a signal duty cycle or a portion of the duty cycle, or to zoom out on the waveform 804 to view a single or multiple duty cycles of the programmed INS.

As previously indicated, the INS duty cycle parameters may also include, in some examples, ramp up parameters for controlling the transition from the stimulation OFF time to the stimulation ON time and/or ramp down parameters for controlling the transition from the stimulation ON time to the stimulation OFF time. FIG. 8B illustrate ramp up and ramp down portions. Some embodiments may provide a visual indication to depict the timing of a ramp up portion of INS stimulation ON times. Some examples may provide a visual indication to depict the timing of a ramp down portion of INS stimulation ON times. Some examples may simply provide an indication if a ramp up transition and/or ramp down transition is being implemented. For example, a step up function may indicate no ramp up transition, and a step down function may indicate no ramp down transition. The inclusion of a ramp up portion may simply indicate that the duty cycle parameters include a ramp up transition, but the slope and duration of the ramp do not necessarily follow the ramp up parameters. Similarly, the inclusion of a ramp down portion may simply indicate that the duty cycle parameters include a ramp down transition, but the slope and duration of the ramp do not necessarily follow the ramp down parameters. Some examples may illustrate the timing of the ramp up and/or ramp down parameters. By way of example and not limitation, the moving or static waveform 804 may illustrate the beginning and duration of a ramp up portion and the increasing slope of the ramp up portion to the beginning of ISN stimulation ON times; and/or the moving or static waveform 804 may illustrate the decreasing slope of a ramp down portion from the ending of ISN stimulation ON times and the duration and ending of the ramp down portion.

Figure 9A:
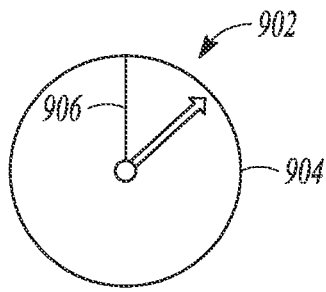
FIGS. 9A-9D illustrate, by way of example, embodiments of a visual indication to depict timing of a neural stimulation therapy such as a programmed INS.
Figure 9B:

FIGS. 9A-9D illustrates an example of a visual indication to depict timing for a programmed INS. As an example, the visual indication can be configured as a circle 902 with a rotating marker 904 as illustrated in FIG. 9A, similar to an analog clock with a rotating hand, to depict the cyclical character of a programmed duty cycle. The circle may include a reference point 906 for the duty cycle, such as the beginning of a stimulation ON time. The circle may include areas of a different shade or color to graphically illustrate a portion of the duty cycle corresponding to a stimulation ON time and another portion of the duty cycle corresponding to a stimulation OFF time. In another example, the visual indication can be configured similar to a digital clock as illustrated in FIG. 9B. For example, the clock may represent minutes and seconds. The clock can indicate the time elapsed of a particular stimulation ON time stage or stimulation OFF time stage of the INS in addition to (or alternatively) the time remaining for the particular ON or OFF time stage to complete.

Figure 9C:
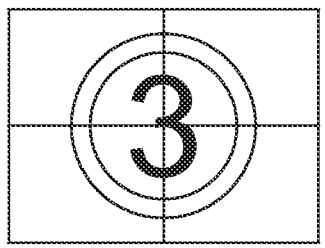

In another example, the visual indication can be configured as a countdown timer such as illustrated in FIG. 9C. In an example, the countdown timer can indicate such as a timing countdown indicative of time left for the completion of a particular state of the duty cycle such as the stimulation ON or stimulation OFF state. For example, the countdown timer 902 in the FIG. 9 indicates "3" which can indicate that the current state (e.g. stimulation ON) state will complete in 3 units of time such as 3 seconds or any other. The time remaining may be displayed. Additionally, the display may flash for each second or otherwise enhance the visual representation of the countdown. The display also may change the brightness or color or other representation as the countdown gets closer to the end. For example, the display may be a first color during a first portion of the count down, and then switch to another color during a second portion of the countdown (e.g. last "x" seconds). In another example, the displayed number can also represent the time remaining to start the next state such as the OFF state of the INS. Different color schemes or shading may be used to distinguish a countdown to a transition from stimulation OFF to stimulation ON, than a countdown to a transition from stimulation ON to stimulation OFF. Some embodiments may change a textual description associated with the counter changes depending on delivery status. By way of example and not limitation, "Time remaining in ON period" may change to "Time till next ON period."

Figure 9D:
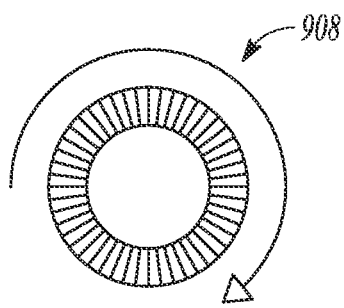

In another example, the visual indication can be configured as a sweep timer as illustrated in FIG. 9D. The sweep timer can include a circular dial and a marker that can be configured to sweep across the circular dial to indicate the progress of the duty cycle of the programmed INS. The area swept at a current time by the marker on the dial can indicate the time elapsed of the therapy or the ON stimulation time or the OFF stimulation time. In an example, a color or a shading of the dial changes to indicate the duty cycle timing. The particular color or shade can be indicative of a particular ON or OFF state of the INS. In some example, multiple portions of the display can indicate multiple countdown timings associated with such as ON and OFF stimulation timing. The multiple portions can in an example be shaded differently to associate the different countdown timings with different timings. In an example, the sweeping of the marker may be disabled when the therapy delivery is disabled.

The visual identification may be implemented using other techniques. For example, the visual indication may be provided by journaling, where the stimulation status is identified (e.g. printed) on a real-time strip.

Some embodiments may automatically adjust the visual indication to adapt to changes in duty cycle. For example, if the stimulation changed from 10 seconds ON/50 seconds OFF to 5 seconds ON/5 seconds OFF, then by way of example 806 in FIG. 8 may automatically expand and 808 in FIG. 8 may automatically shrink to reflect the new duty cycle ratio. That is, for this specific example, the indicator may be automatically adjusted to reflect a change from the old ON/OFF ratio of 20% to the new ON/OFF ration of 50%.

Figure 10:
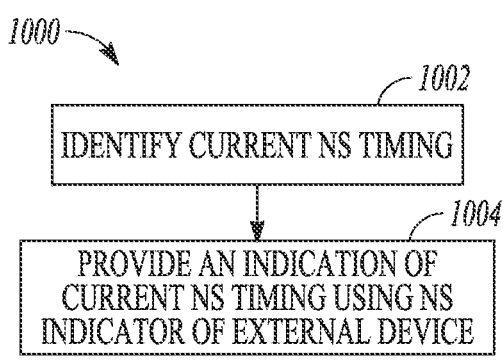
FIG. 10 illustrates, by way of example, an embodiment of a method for providing an indication of the current INS timing of the programmed INS.

FIG. 10 illustrates, by way of example, a method 1000 for providing an indication of current timing of the programmed neural stimulation (NS) to the clinician. At 1002, current timing of the programmed NS can be identified. In an example, the programmed NS includes a programmed INS therapy with alternating stimulation ON and stimulation OFF times, and timing for delivering stimulation bursts of a plurality of stimulation pulses during the stimulation burst ON times. The identification of the current timing can include a marker for identifying a state of the INS. In an example, the programmed INS include a duty cycle with a stimulation ON time and a stimulation OFF time, and the identification of the current timing can include identification of a phase or a state of the duty cycle. In an example, the IMD 104 can be configured to communicate the current timing of the programmed INS to the external device 118. The IMD 104 may provide the external device with its programmed timing characteristics (e.g. INS duty cycle parameters). In an example, the external device 118 can be used to detect the current timing of the INS. The external device 118 can include such as a timer or timekeeping device to identify the current timing of the programmed INS. The external device may be programmed with the known timing characteristics (e.g. INS duty cycle parameters) of the NS delivered by the IMD. The external device may be programmed with a "learning mode" to monitor and detect a pattern the NS delivered by the IMD, and derive the timing characteristics (e.g. duration of the stimulation ON period and duration of the stimulation OFF period for a consistently-delivered INS).

At 1004, an indication of the current timing of the programmed INS can be provided to the physician using an INS indicator of the external device 118. In an example, providing the indication of the current timing of the programmed INS can include providing an indication that the programmed INS is currently in a stimulation ON state or stimulation OFF state. In an example, other indications such as an indication of a current phase of the INS, a time until the next transition (stimulation ON to stimulation OFF and/or stimulation OFF to stimulation ON). The indication of the current timing of the INS can be provided using any of the audible or visual indications as discussed previously.

Figure 11:
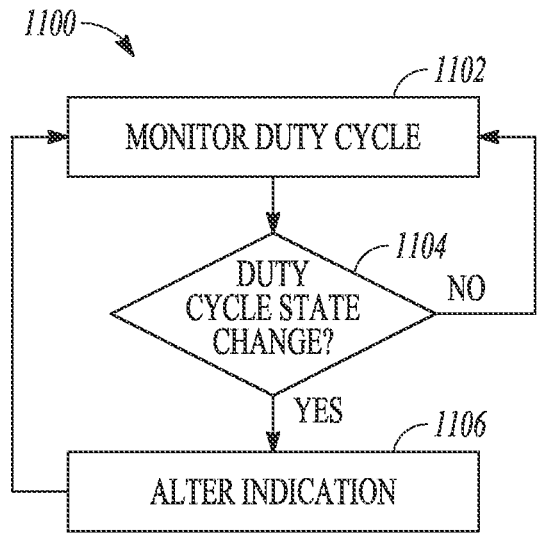
FIG. 11 illustrates, by way of example, an embodiment of a method for indicating a change in a state of the duty cycle.

FIG. 11 illustrates, by way of an example, a method 1100 for indicating a change in a state of the duty cycle of the programmed INS. At 1102, the duty cycle of the programmed INS can be monitored. In an example, the duty cycle of the programmed INS can include alternating stimulation ON and stimulation OFF states. The duty cycle for the programmed INS can be determined in terms of a ratio of the duration for the stimulation ON state to a total duration of the stimulation. In an example, this ratio may be expressed as a percentage. For example, a duty cycle of 60% can indicate that the stimulation is ON for 60% of the total stimulation duration and the stimulation is OFF for 40% of the total stimulation duration. In an example, the duty cycle can be monitored such as to identify a change in the state of the duty cycle. For example, the IMD 104 can be configured to monitor the current timings of the programmed INS such as to identify any change from the stimulation ON state to the stimulation OFF state and vice-versa. At 1104, a determination can be made as to whether the state of the duty cycle has changed. The method 1100 can continue to monitor the duty cycle at 1102 when there is no change in the state of the duty cycle.

At 1106, an indication can be altered on detection of the change in the state of the duty cycle. In an example, the indication change can include alteration in the visual indications or audio indications. Examples of alteration in the visual indications can include changing the color of the LED indicator, altering a state of a waveform (e.g., static to moving) or any other change in response to the change in the state of the duty cycle. Examples of alterations in the audio indications can include changing a pitch of an audible tone, turning ON/OFF of the audio, generating different audio tones or any other audio change to indicate corresponding states of the duty cycle. With programmed or derived knowledge about the timing of the duty cycle, an upcoming transition can be predicted, and the indication can be altered as the upcoming transition approaches. For example, a beeping sound during one state (e.g. stimulation OFF) may become faster or louder during the last few seconds before the transition to the other state (e.g. stimulation ON). Similarly, a flashing display may flash quicker or brighter during the last few seconds before a transition.

Figure 12:
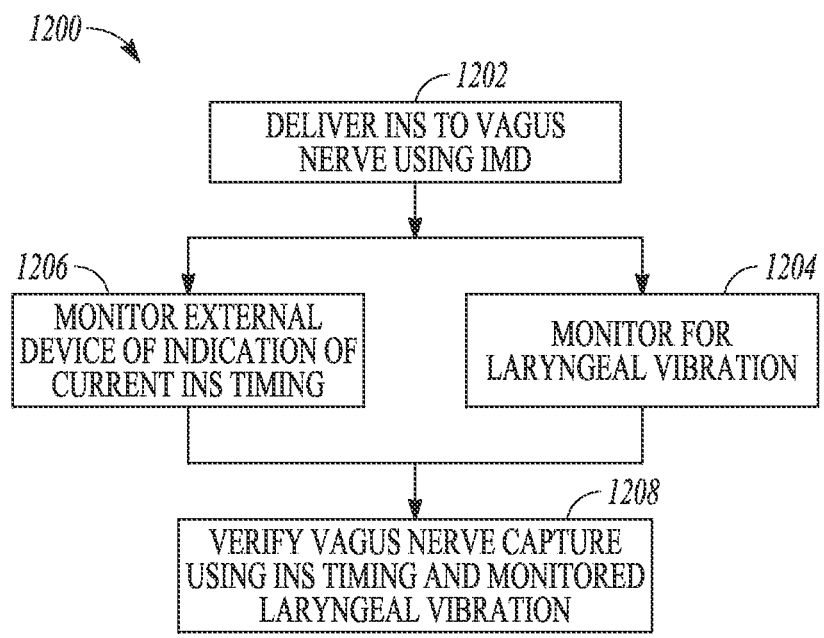
FIG. 12 illustrates, by way of an example, a method for verifying capture of the vagus nerve.

FIG. 12 illustrates, by way of an example, a method 1200 for verifying capture of the vagus nerve while delivering the neural stimulation therapy to the patient. At 1202, the neural stimulation therapy can be delivered to the vagus nerve 112 of the patient 102 using the IMD 104. In an example, IMD 104 can be programmed to deliver a programmed INS therapy with alternating stimulation ON and stimulation OFF times and timing for delivering stimulation bursts of a plurality of stimulation pulses during the stimulation burst ON times. At 1204, the laryngeal vibrations can be monitored, such as by the physician while delivering the neural stimulation therapy. In an example, the physician can sense the laryngeal vibrations by physically touching the patient's neck. At 1206, the physician also monitors the external device for an indication of the current INS timing such as whether the programmed INS is in a state of the stimulation ON time or in a state of the stimulation OFF time. In an example, monitoring the external device 118 for indication can include monitoring the indication to detect an upcoming transition in the programmed INS between stimulation ON time and stimulation OFF time. In an example, monitoring the external device 118 can include monitoring the phase of the cycle of programmed INS.

In some examples, based on the results of monitoring of the laryngeal vibrations and indications regarding the current INS timing on the external device 118, at 1208, the capture of the vagus nerve 112 can be verified. For example, the physician can determine that the programmed INS is capturing the vagus nerve 112 when the laryngeal vibrations are detected during the stimulation ON time of the programmed INS. In an example, the physician can determine that the programmed INS is not capturing the vagus nerve 112 when the laryngeal vibrations are not detected during the stimulation ON time of the programmed INS.

Thus, by way of example, the present subject matter provides the clinician better guidance as to when to look for laryngeal vibration without requiring real-time streaming of physiological data. However, physiological data may be used to correlate physiologic changes to changes in the delivery of the therapy. Thus, some embodiments may further provide one or more physiological sensors. Examples of such physiological sensors may include, but are not limited to a heart rate sensor, a blood pressure sensor, a respiration sensor. One or more physiological sensors may be implanted with the IMD providing the neural stimulation. One or more physiological sensor(s) may be implanted in another location and/or may be part of another implantable device such as an implantable cardiac rhythm management (CRM) device. Examples of implantable CRM devices include pacemakers, cardioverters, and defibrillators. An implantable CRM device may be configured to deliver cardiac resynchronization therapy (CRT) for a heart failure patient. One or more physiological sensor(s) may be external. For example, an external blood pressure cuff may be used. In other example, external sensors may be used to sense an electrocardiogram or may be used to sense respiration characteristics.

Physiological data sensed by the sensor(s) may be used to provide additional context to therapy delivery even if alone the physical data may not be enough to determine when therapy is actually being delivered. Applicant incorporates U.S. Published Patent Application 20060241725 entitled "Method and Apparatus for Simultaneously Presenting Cardiac and Neural Signals", and U.S. Pat. No. 7,640,057 entitled "Methods of Providing Neural Markers for Sensed Autonomic Nervous System Activity" by reference in their entirety.

By way of example, the additional context may provide insight into not only whether stimulation is being delivered, but whether the stimulation is capturing motor fibers (e.g. motor fibers in the vagus nerve that cause laryngeal vibration), whether the stimulation is causing a cough reflex, or whether the stimulation is effecting a physiological response such as a change in heart rate or blood pressure. For example, a patient with a consistent cough may be monitored to determine if it occurs at the start or at the end of therapy delivery. If so, then a ramp up (stimulation OFF to stimulation ON) or ramp down (stimulation ON to stimulation OFF) stimulation protocol may be implemented or adjusted. If the cough consistently occurs after a certain duration of therapy delivery, then it may be appropriate to alter the duty cycle of the stimulation. The clinician may choose to tie the stimulation to portions of the respiration cycle. In another example, it may be observed that a hypertension therapy is effective but wanes after a certain period of time (e.g. 90 seconds) after delivery, then it may be appropriate to change to a duty cycle of 90 seconds ON/10 seconds OFF to provide a better average reduction in BP. In another example, it may be observed that hypertension therapy is effective and reaches stable blood pressure after one minute delivery, and then has a hysteresis of "n" seconds of no therapy before blood pressure starts to elevate. Further, by way of example, having physiologic data overlaid can help determine if chronically 20 seconds ON/5 seconds OFF maintains blood pressure but 20 seconds ON/7 seconds OFF creates too much variation in blood pressure as blood pressure starts to rise after 5 seconds of no therapy delivery. The indicator allows the clinician to note correlations between the stimulation and the physiological response. This in turn provides the clinician with more insight into how to adjust the stimulation to enhance desired physiological response(s) and/or avoid undesired physiological response(s).

The above detailed description is intended to be illustrative, and not restrictive. Other embodiments will be apparent to those of skill in the art upon reading and understanding the above description. The scope of the invention should, therefore, be determined with reference to the appended claims, along with the full scope of equivalents to which such claims are entitled.

What is claimed is:

1. A system, comprising:
    an implantable medical device (IMD) configured to deliver programmed intermittent neural stimulation (INS) to a vagus nerve of a patient, wherein the programmed INS includes:
        alternating stimulation ON and stimulation OFF times; and
        timing for delivering stimulation bursts of a plurality of stimulation pulses during the stimulation burst ON times; and
    an external device configured to identify current timing of the INS delivered by the IMD, the external device including an INS indicator configured to provide a user-perceptible indication of the current timing of the INS, wherein the user-perceptible indication comprises a first audible signal during the stimulation ON times and a second audible signal during the stimulation OFF times, and wherein the first audible signal is different from the second audible signal.

2. The system of claim 1, wherein to identify the current timing the external device is configured to determine when the programmed INS transitions between the stimulation ON and stimulation OFF times, and wherein the INS indicator is configured to indicate when the programmed INS transitions between the stimulation ON and stimulation OFF times.

3. The system of claim 1, wherein to identify the current timing the external device is configured to determine a time until a next stimulation ON time, and wherein the INS indicator is configured to indicate the time until the next stimulation ON time.

4. The system of claim 1, wherein to identify the current timing the external device is configured to determine a time until a next stimulation OFF time, and wherein the INS indicator is configured to indicate the time until the next stimulation OFF time.

5. The system of claim 1, wherein:
the INS includes a cycle of the stimulation ON and stimulation OFF times;
to identify the current timing the external device is configured to determine a phase of the cycle; and
the INS indicator is configured to indicate the phase of the cycle.

6. The system of claim 1, wherein the IMD is configured to send a communication signal to the external device, and the external device is configured to use the communication signal to identify the current timing of the INS delivered by the IMD.

7. The system of claim 1, wherein to identify the current timing of the INS delivered by the IMD, the external device is configured to detect a timing for delivering stimulation bursts of a plurality of stimulation pulses during stimulation burst ON times.

8. The system of claim 1, wherein the INS indicator is configured to provide an audible signal to indicate an approaching transition between the stimulation ON and stimulation OFF times.

9. The system of claim 8, wherein the audible signal to indicate an approaching transition between the stimulation ON and stimulation OFF times comprises increasing a frequency of the intermittent audible signal.

10. The system of claim 1, wherein the INS indicator is configured to visibly identify the current timing of the INS.

11. The system of claim 1, wherein the INS indicator is configured to provide a visible signal to indicate whether the programmed INS is currently in a stimulation ON time or to indicate whether the programmed INS is currently in a stimulation OFF time.

12. The system of claim 1, wherein the INS indicator is configured to provide a visual representation of an INS waveform, wherein the visual representation of the INS waveform is configured to indicate a current timing of the INS.

13. The system of claim 1, wherein the system is configured to facilitate:
monitoring the external device for an indication of the current timing of the INS;
monitoring for laryngeal vibration; and
using monitored laryngeal vibration results and the indication of the current timing of the INS to determine if the INS is capturing the vagus nerve, wherein using monitored laryngeal vibration results and the indication of the current timing of the INS to determine if the INS is capturing the vagus nerve includes determining that the INS is not capturing the vagus nerve when laryngeal vibration is not detected and the current timing of the INS is stimulation ON.

14. The system of claim 13, wherein the step of monitoring for laryngeal vibration is performed by a user physically touching the patient's neck.

15. The system of claim 1, wherein the first audible signal is continuous and the second audible signal is intermittent.

16. A method, comprising:
identifying current timing of an intermittent neural stimulation (INS) programmed in an implantable medical device, wherein the programmed INS includes:
alternating stimulation ON and stimulation OFF times; and
timing for delivering stimulation bursts of a plurality of stimulation pulses during the stimulation burst ON times;
providing an indication of the current timing of the INS using an INS indicator of an external device, wherein the user-perceptible indication comprises a first audible signal during the stimulation ON times and a second audible signal during the stimulation OFF times, and wherein the first audible signal is different from the second audible signal;
monitoring the external device for the INS indicator;
monitoring for laryngeal vibration; and
using monitored laryngeal vibration results and the INS indicator to determine if the INS is capturing the vagus nerve, wherein using monitored laryngeal vibration results and the INS indicator to determine if the INS is capturing the vagus nerve includes determining that the INS is not capturing the vagus nerve when laryngeal vibration is not detected and the current timing of the INS is stimulation ON.

17. The method of claim 16, wherein providing an indication of the current timing of the INS includes providing a visual indication of the current timing of the INS.

18. The method of claim 16, wherein the INS includes a cycle of the stimulation ON and stimulation OFF times, and providing an indication of the current timing of the INS includes providing an indication of a phase of the cycle.

19. A system, comprising:
an implantable medical device (IMD) configured to deliver programmed intermittent neural stimulation (INS) to a vagus nerve, wherein the programmed INS includes:
alternating stimulation ON and stimulation OFF times; and
timing for delivering stimulation bursts of a plurality of stimulation pulses during the stimulation burst ON times; and
an external device configured to identify current timing of the INS delivered by the IMD, the external device including an INS indicator configured to provide a user-perceptible indication of the current timing of the INS, wherein the user-perceptible indication comprises an intermittent audible signal during the stimulation OFF times, and wherein INS indicator is configured to increase a frequency of the intermittent audible signal indicate an approaching transition between the stimulation OFF and stimulation ON times.

20. The system of claim 19, wherein the user-perceptible indication further comprises a continuous audible signal during the stimulation ON times.

* * * * *